United States Patent
Sattig et al.

(10) Patent No.: US 10,751,681 B2
(45) Date of Patent: Aug. 25, 2020

(54) MIXING DEVICE, IN PARTICULAR DESIGNED FOR MIXING BONE CEMENT

(71) Applicant: aap Biomaterials GmbH, Dieburg (DE)

(72) Inventors: Christoph Sattig, Dieburg (DE); Stefan Deusser, Karlstein (DE); Rike Anders-Wessel, Oberursel (DE)

(73) Assignee: OSARTIS GmbH, Dieburg (DE)

( * ) Notice: Subject to any disclaimer, the term of this patent is extended or adjusted under 35 U.S.C. 154(b) by 18 days.

(21) Appl. No.: 15/500,420

(22) PCT Filed: Jun. 18, 2015

(86) PCT No.: PCT/EP2015/063731
§ 371 (c)(1),
(2) Date: Jan. 30, 2017

(87) PCT Pub. No.: WO2016/020097
PCT Pub. Date: Feb. 11, 2016

(65) Prior Publication Data
US 2017/0239631 A1     Aug. 24, 2017

(30) Foreign Application Priority Data
Aug. 4, 2014   (DE) .................. 10 2014 111 035

(51) Int. Cl.
| | |
|---|---|
| *B01F 15/02* | (2006.01) |
| *A61B 17/88* | (2006.01) |
| *B01F 3/14* | (2006.01) |
| *B01F 15/00* | (2006.01) |
| *B01F 13/00* | (2006.01) |
| *A61B 17/00* | (2006.01) |

(52) U.S. Cl.
CPC ...... *B01F 15/0212* (2013.01); *A61B 17/8833* (2013.01); *B01F 3/14* (2013.01);
(Continued)

(58) Field of Classification Search
CPC .............. B01F 13/0023; B01F 15/0225; B01F 15/0226; A61J 1/2089; A61B 17/8825;
(Continued)

(56) References Cited

U.S. PATENT DOCUMENTS

| | | | |
|---|---|---|---|
| 3,767,085 A | 10/1973 | Cannon et al. | |
| 5,569,210 A * | 10/1996 | Moen ............... | A61B 5/150038 600/573 |

(Continued)

FOREIGN PATENT DOCUMENTS

| | | |
|---|---|---|
| DE | 69715007 T2 | 4/2003 |
| DE | 102009013211 B4 | 4/2012 |

(Continued)

OTHER PUBLICATIONS

"International Search Report and Written Opinion" issued in counterpart PCT application No. PCT/EP2015/063731, dated Feb. 11, 2016, Publisher: PCT.

(Continued)

*Primary Examiner* — Elizabeth Insler
(74) *Attorney, Agent, or Firm* — Kaplan Breyer Schwarz, LLP (57) ABSTRACT

A mixing device, in particular for bone cement, in which at least two ampoules provided with a septum are pushed onto needles, in parallel to each other, for discharging the liquid.

3 Claims, 11 Drawing Sheets

(52) U.S. Cl.
CPC ...... *B01F 13/0023* (2013.01); *B01F 15/0087* (2013.01); *B01F 15/0226* (2013.01); *A61B 2017/00495* (2013.01); *A61B 2017/8838* (2013.01); *B01F 2215/0029* (2013.01)

(58) Field of Classification Search
CPC ...... A61B 2050/0083; A61B 5/150351; A61B 17/8833; B05C 17/00506; A61M 5/2448
See application file for complete search history.

(56) References Cited

U.S. PATENT DOCUMENTS

| 2012/0172830 A1* | 7/2012 | Yokoyama | A61J 1/2089 604/413 |
| 2014/0021076 A1* | 1/2014 | Soma | A61J 1/2089 206/219 |
| 2014/0192611 A1 | 7/2014 | Sasaki et al. | |
| 2015/0117140 A1* | 4/2015 | Asada | A61B 17/00491 366/176.3 |

FOREIGN PATENT DOCUMENTS

| WO | 2011139921 A2 | 11/2011 |
| WO | 2013179832 A1 | 12/2013 |

OTHER PUBLICATIONS

Officer: Nora Lindner, "International Preliminary Report on Patentability and English Translation", International atent Application PCT/EP2015/063731, Report Completed Feb. 7, 2017, p. 20.

* cited by examiner

MIXING DEVICE, IN PARTICULAR DESIGNED FOR MIXING BONE CEMENT

FIELD OF THE INVENTION

The invention relates to a mixing device which is in particular configured for mixing bone cement.

BACKGROUND OF THE INVENTION

Mixing devices, in particular mixing devices for mixing components of medical products such as bone cement, for example, are known.

In a two-component system, two substances, in particular a liquid and a solid, are mixed together before being used, can be processed for a short period of time and will then cure.

In the medical field, in particular mixing devices for methyl methacrylate-based bone cement are known. Usually, a PMMA powder is mixed with a monomer component so that a curable paste is prepared. This paste is usually processed very well and is in particular used for cementing prostheses.

German patent DE 10 2009 013 211 B4 discloses such a generic mixing device.

In this embodiment variant of a bone cement mixer, the monomer component is disposed on a handle of the mixing system. Before use, a monomer vial is pressed onto a needle. Due to a gas volume present in the monomer vial and due to a vacuum applied to the mixing chamber, the monomer flows into the mixing chamber.

Such a closed system is simple in design and safe in handling.

A drawback thereof is that highly volatile monomer components such as methyl methacrylate are only allowed to be transported in relatively small packages, depending on the applicable legal situation. In the case of the initially mentioned mixing device this might for some applications undesirably limit the quantity that can be mixed using the mixing device.

Furthermore, the aforementioned system is only configured for mixing together a liquid component and a solid component. The system is not intended for mixing two monomer components each one contained in a respective vial, which may moreover comprise a different liquid.

OBJECT OF THE INVENTION

Given this background, the object of the invention is to provide a mixing device, in particular a mixing device for bone cement, which is easier and even more safe in handling.

SUMMARY OF THE INVENTION

The object of the invention is already achieved by a mixing device in accordance with the illustrative embodiment of the present invention.

Firstly, the invention relates to a mixing device which is in particular configured for bone cement.

It comprises at least two ampoules filled with a liquid. Any suitable type of container can be used as an ampoule. In particular, the invention relates to glass ampoules in the form of vials provided with a septum that can be perforated.

According to the invention, two ampoules filled with a liquid can be perforated by means of needles and the liquid contained in the ampoules can be discharged through the needles, and the ampoules can be simultaneously pushed onto the needles using an ampoule holder.

Thus, according to the invention two ampoules are simultaneously pushed onto a respective needle so that the liquid from the two ampoules flows out simultaneously.

This has some advantages compared to a mixing device with only one ampoule. For example, the package size of the individual ampoules can be reduced, if necessary.

Furthermore, it is conceivable to mix two different liquids by means of the mixing device, by combining them during or after extraction.

Moreover, depending on the desired amount of bone cement to be mixed, it is conceivable to load the mixing device with only one or with two or more ampoules.

Preferably, the mixing device furthermore comprises a mixing chamber to which a vacuum can be applied. The liquid flows from the ampoules into the mixing chamber.

This may be accomplished, for example, by means of a tube which can additionally be used for pressing out the bone cement from the mixing chamber after mixing, by separating a housing containing the ampoules from the remaining mixing device, or for actuating a paddle arranged in the mixing chamber.

Preferably, the liquid flows out of the ampoules due to a gas volume included in the ampoules. However, it is also conceivable to ventilate the ampoules, for example via a diaphragm valve, or to provide needles in a thickness which permit air bubbles to ascend through the needles to enable pressure exchange in this way.

The use of at least two ampoules moreover offers the advantage that emptying occurs faster.

In one embodiment of the invention, the ampoule holder is arranged in a cap which can be slideably inserted into a housing that comprises the needle.

The cap may in particular be slideably latched in a housing, and the ampoule holder is accommodated in the cap as a separate component, for example also by being latched thereto.

However, a variant in which the ampoule holder is an integral component of the cap is also conceivable, so that the cap then supports the ampoules.

Preferably, the mixing device comprises a manifold. This manifold has passages in communication with the needles. Within the manifold, the liquids from the at least two ampoules are combined and can then be discharged via a channel, such as a tube.

The invention furthermore relates to a mixing device, in particular a mixing device as described above.

It comprises at least one ampoule filled with a liquid, which is opened by pushing the ampoule onto an opening means. The opening means is in particular provided in the form of a needle.

However, a different form is also conceivable, for example the form of a mandrel which does not have a passage but is adapted to open the ampoule so that the liquid can exit past the opening means.

According to the invention, an unlocking means must be actuated for being able to push the ampoule. This means that the ampoule holder can only be pushed in the direction of the opening means when the unlocking means are simultaneously actuated. In its engaged position on the opening means the ampoule is latched non-detachably.

In contrast to the prior art mentioned above, in which a safety bolt is removed, the unlocking means may thus constitute an integral part of the housing of the mixing device, and therefore the unlocking means will not produce any small parts which might present a potential danger in the operating room.

The at least one ampoule is preferably arranged in a cap, which is slideably accommodated in the housing and projects beyond the housing in its non-engaged position.

In the engaged and latched position, it is easy for the user to recognize that the mixing device was already used, given the compressed state of the housing.

The latching moreover ensures that the entire liquid is discharged, since the user can not stop the discharging of the liquid by retracting the ampoule.

The invention furthermore relates to a mixing device, in particular one as described above.

It comprises at least one ampoule filled with a liquid, which is opened by pushing the ampoule onto a needle in order to discharge the liquid.

According to the invention, the needle is made of plastics.

The plastic needle in particular constitutes an integral part of an insert which is inserted in a housing of the mixing device and which is connected to the housing of the mixing device, for example by welding or gluing.

It has been found that with such an insert a plastic needle which is sufficient for piercing a monomer vial that is provided with a septum can be provided as an integral component of the insert.

This has considerable advantages in terms of production technology, since a single injection-molded part can be used to provide the needle and the insert. In particular it is not necessary to fit a metal cannula in the injection mold, which makes manufacturing faster and cheaper.

The insert is in particular provided in the form of a manifold comprising at least two needles.

It is preferably formed of two pieces, consisting of a needle unit with the two plastic needles and a manifold which includes passages for combining the liquids from the two needles.

The invention further relates to a mixing device, in particular one as described above.

It comprises at least one ampoule filled with a liquid. The ampoule can be opened by being pushed onto an opening means, in particular a needle, for discharging the liquid.

According to the invention, the ampoule is accommodated in an ampoule holder which is arranged in a cap which in turn is slideably inserted in a housing. The housing comprises at least one opening means and a channel for discharging the liquid.

Thus, the casing for accommodating the ampoule comprises three main components, namely a housing which may be considered as a main housing and which, for example, comprises a tube for discharging the liquid and the opening means.

In contrast to the prior art mentioned above, the ampoule is not inserted directly into the cap, but is supported by an ampoule holder inserted into the cap.

This provides for simplified assembly on the one hand.

On the other hand, the ampoule holder is preferably configured so as to comprise at least one retaining member engaging the ampoule at a collar to hold it in a defined position.

The ampoule may in particular be snapped into the retaining member.

The retaining member ensures a defined position of the ampoule relative to the opening means.

The invention is based on the findings that for example for known ampoules provided with a septum, the septum or the cap by which the ampoule is sealed has small tolerances.

Irrespectively of whether the retaining member engages the cap itself or a collar of the ampoule preferably made of glass, a high degree of dimensional accuracy will always be achieved.

The length of conventional glass vials, by contrast, is subject to rather high tolerances which can not always be reliably compensated by the configuration of the mixing device if the position of the ampoule in the cap is determined by the rear end of the ampoule.

In a preferred embodiment of the invention, the ampoule holder and the cap are latched together, and the cap and housing are latched together as well.

The assembly of such a three-part casing for the ampoule is thus accomplished very easily.

DETAILED DESCRIPTION

The subject matter of the invention will now be explained in more detail with reference to an exemplary embodiment illustrated in FIGS. 1 to 14.

Figure 1:
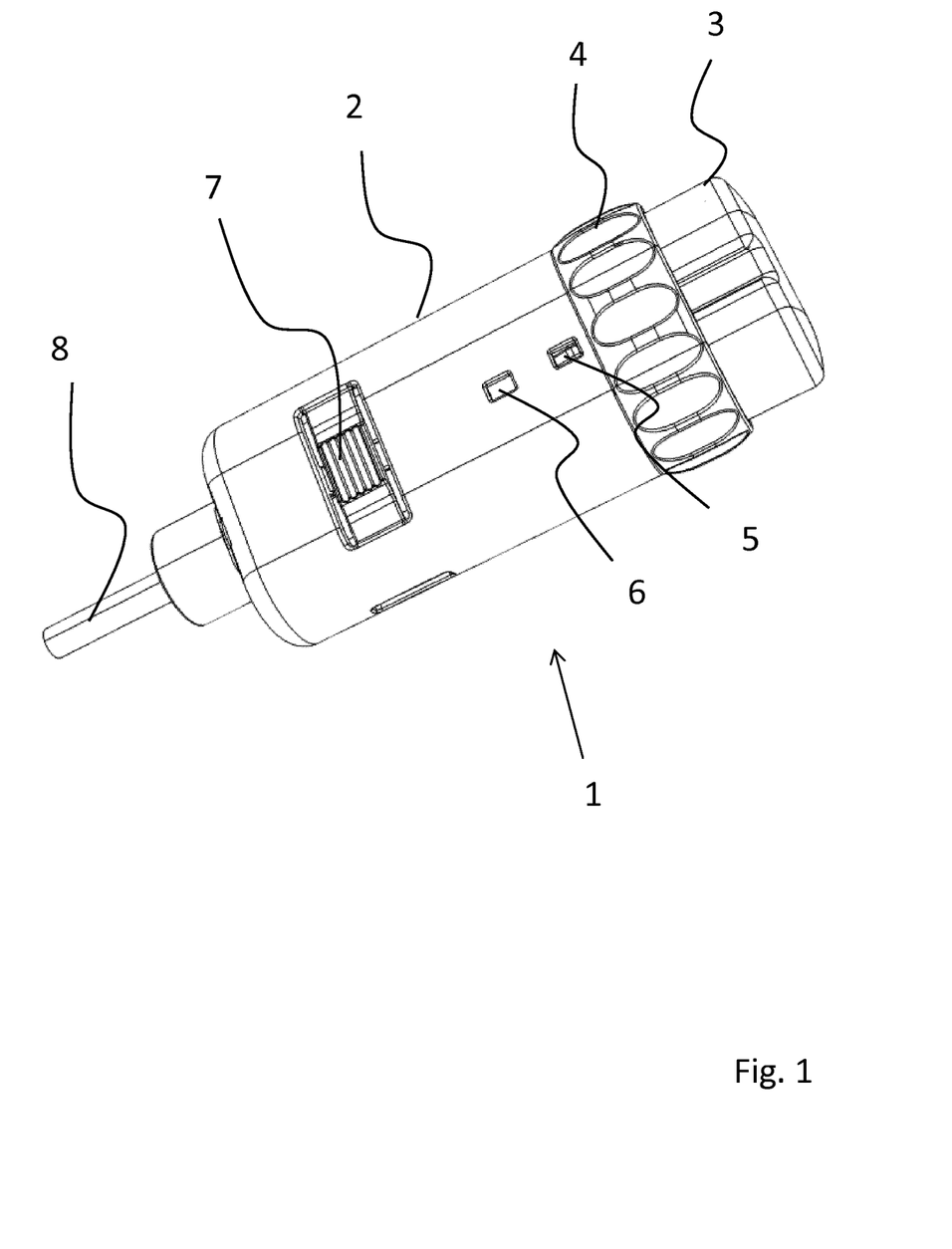
FIG. 1 is a perspective view of a mixing device.

FIG. 1 is a perspective view of a mixing device 1.

Mixing device 1 comprises a housing 2 which in this exemplary embodiment is elongated and has a cross section that is substantially rectangular with rounded corners, or oval.

The shape of the housing different from a circular cylindrical shape allows to safely grip the housing, in particular when using the housing which accommodates the ampoules.

For actuating a mixer, the necessary push and pull movements with simultaneous rotation of the mixing paddle can be performed more easily.

A cap 3 is slideably accommodated in the housing 2, which is depressed to discharge the liquid.

The housing 2 has a profiled surface area 4 which is intended to provide an even better grip. Such a profiled surface may be particularly advantageous when the housing illustrated herein is used for driving a paddle for mixing bone cement in a mixing chamber (not shown).

A unlocking means 7 in the form of a button or pushbutton can be seen, which is provided in mirror-symmetrical manner in this embodiment of the invention, that is to say also on the opposite side.

Furthermore, a first opening 5 and a second opening 6 can be seen in housing 2.

In an actuated state, a snap projection of cap 3 is latched in opening 5 and prevents cap 3 from being retracted rearwards.

When the user now actuates the unlocking means 7 on both sides by depressing them, he or she can push the cap 3 further forward or press it deeper into the housing 2, and a snap projection on cap 3 will then become latched in the opening 6 in an actuated state.

The liquid from the ampoules accommodated in housing 2 will then exit via tube 8.

When used as a bone cement mixing device, tube 8 is connected to a mixing chamber (not illustrated) to which a vacuum is applied and in which a solid component is mixed with the liquid from the ampoules.

In this case, the housing 2 may be used to drive a mixing paddle. Subsequently, housing 2 can be severed at a predetermined breaking point (not illustrated) of tube 8, for pressing out the bone cement. Moreover, the housing 2 illustrated herein, which is designed for accommodating the monomer ampoule, may furthermore be used as a handle to actuate a plunger to press out the bone cement (not illustrated).

Figure 2:
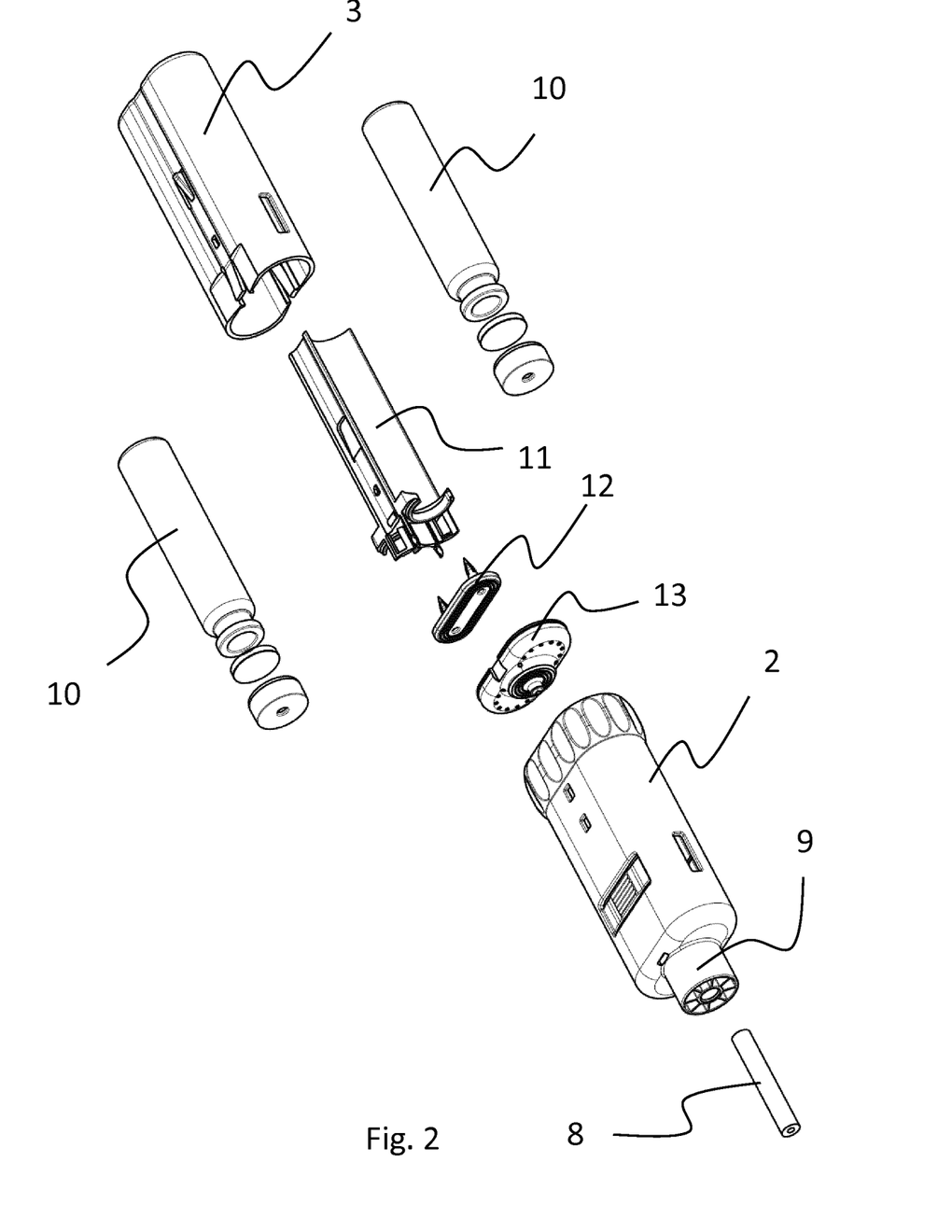
FIG. 2 illustrates the essential components of the mixing device of FIG. 1 in an exploded view.

FIG. 2 illustrates the essential components of the mixing device of FIG. 1 in an exploded view.

Housing 2 can be seen, on which the tube 8 for discharging the liquid is mounted on an extension 9 which has a circular cylindrical shape in this case.

In this exemplary embodiment, the mixing device furthermore comprises two monomer vials 10 which are closed by a septum.

The ampoules 10 containing the monomer are first inserted into an ampoule holder 11.

Then, the ampoule holder 11 is slideably inserted into cap 3 where it becomes latched.

Furthermore, a needle unit 12 can be seen which comprises two needles.

In the assembled state, needle unit 12 is coupled with a manifold 13 which itself is inserted in the housing 2 together with needle unit 12 and is in particular connected thereto by being welded or glued thereto.

If now the cap 3 is pressed down, as already described with reference to FIG. 1, the ampoules 10 will simultaneously be pushed onto the needle unit 12.

The liquid will then flow through the needles of needle unit 12 and through manifold 13 into the tube 8, for example by virtue of a vacuum applied to tube 8 in conjunction with a gas volume in ampoules 10, and will exit into a mixing chamber, for example.

Figure 3:
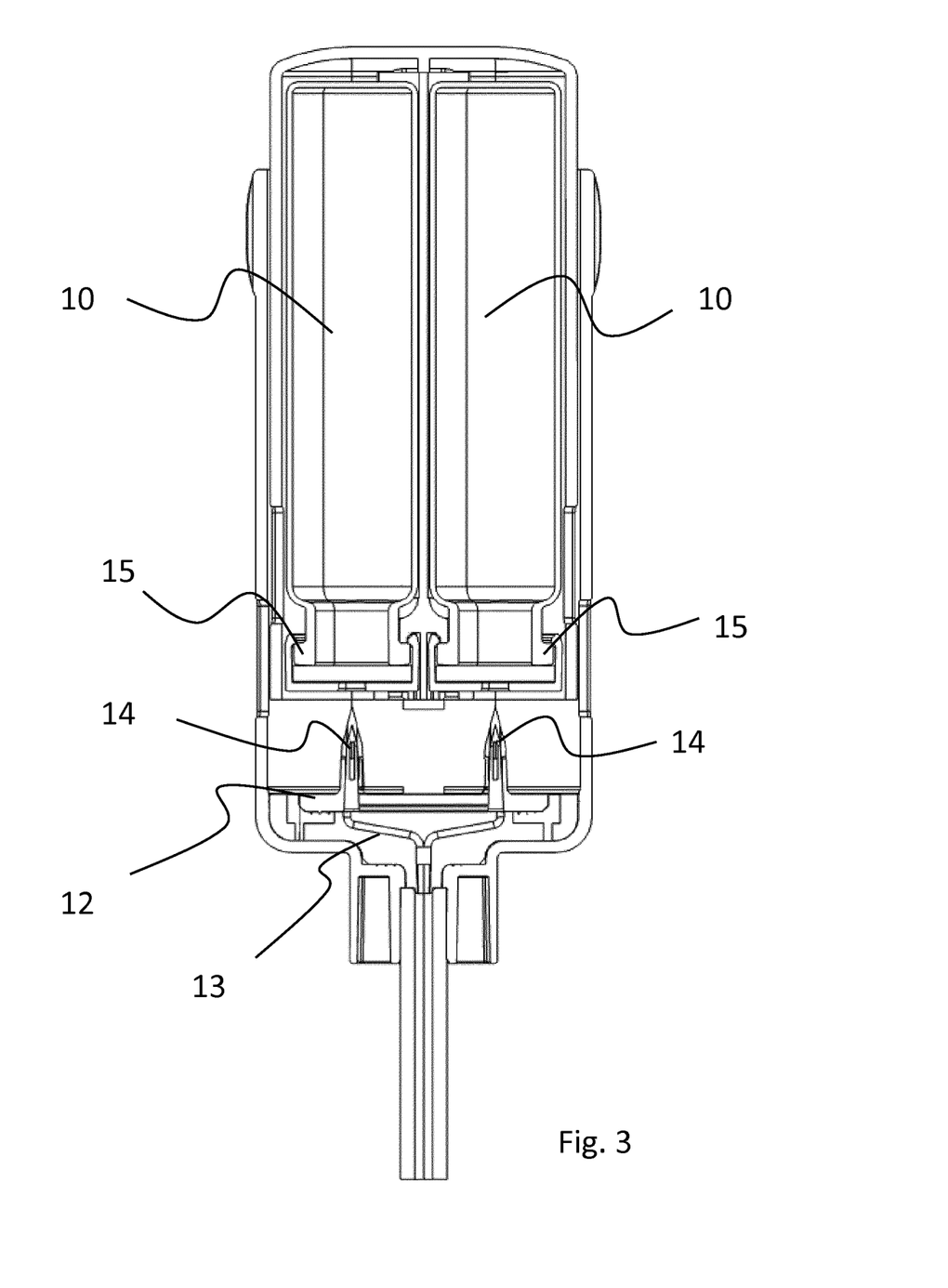
FIG. 3 shows a sectional view of a mixing device in the pre-assembled but not yet actuated state.

FIG. 3 shows a sectional view of a mixing device in the pre-assembled but not yet actuated state.

The two ampoules 10 can be seen, which are arranged in parallel and held on a collar 15 in a defined position.

Needles 14 of needle unit 12 can also be seen. Needle unit 12 is connected to manifold 13 which includes passages where the liquid from the two ampoules 10 is combined.

The system according to the invention may therefore also be used to mix two liquids with each other.

Figure 4:
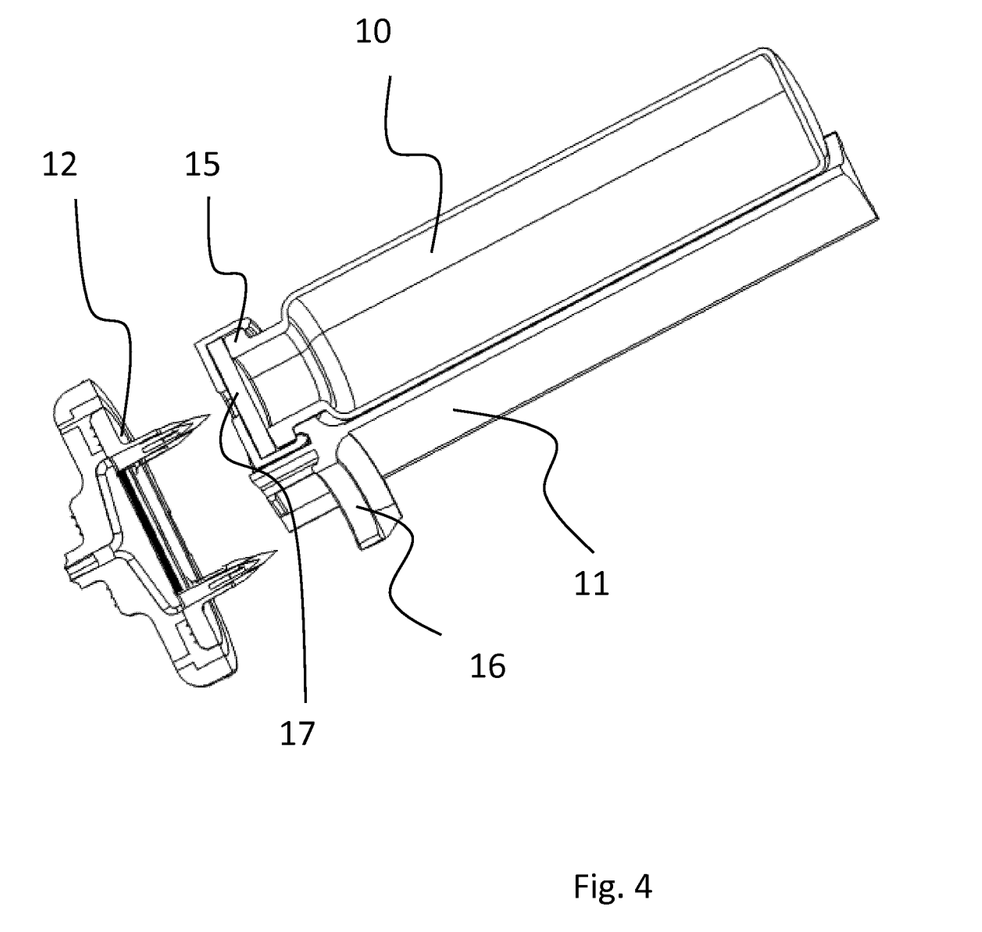
FIG. 4 shows a perspective sectional view in which the housing, the housing cap, and one ampoule are omitted.

FIG. 4 shows a perspective sectional view in which the housing, the housing cap and one ampoule are omitted.

It can be seen that the ampoule 10 has a collar 15 that is seated in a retaining member 16 of an ampoule holder.

Thus, the septum 17 is arranged directly opposite to the needle of needle unit 12.

In addition to the better defined position of the ampoule 10, the use of an ampoule holder provides for improved assembly.

Preferably, the ampoule 10 is snapped into retaining member 16.

Figure 5:
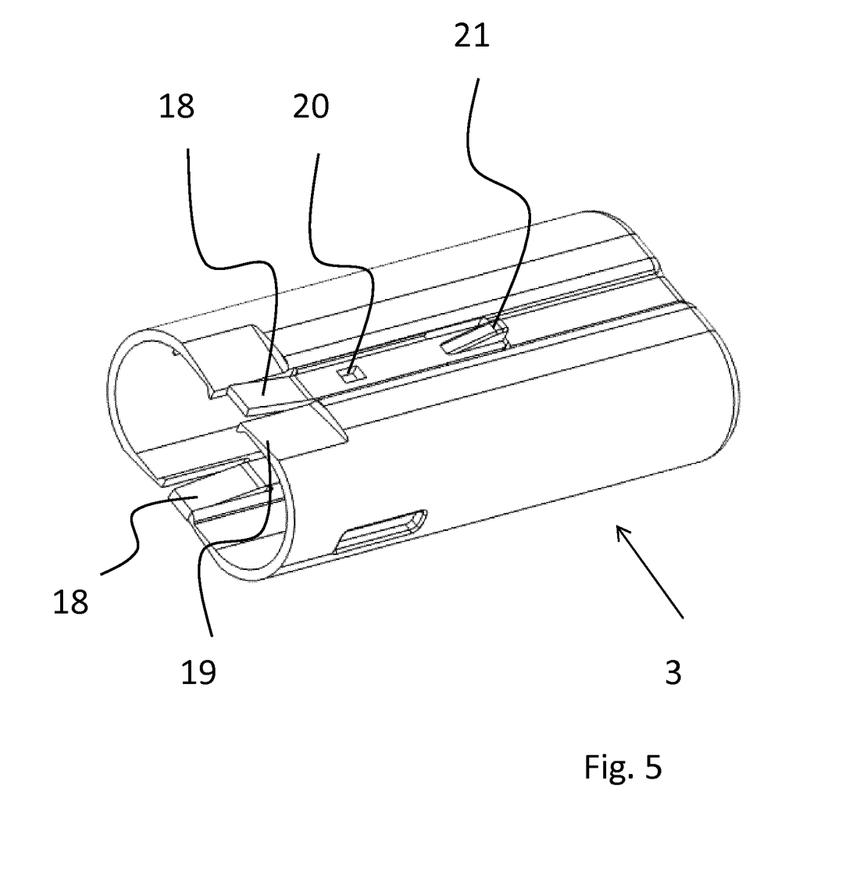
FIG. 5 is a perspective view of the cap.

FIG. 5 is a perspective view of the cap.

The cap is formed for being slideably inserted into the housing (2 in FIG. 1).

The cap has latching tabs 18 which protrude from an adjacent housing wall 19.

Latching tabs 18 can be urged inwards by actuating the unlocking means (7 in FIG. 1) in order to release the cap and hence the ampoules accommodated in the cap to be able to slideably displace them.

Furthermore, the cap has a latching projection 21 which in the pre-assembled but not yet actuated state is latched in the upper opening of the housing (5 in FIG. 1) and which is latched in the lower opening (6 in FIG. 1) in the actuated state.

A further opening 20 in the cap serves to latch the cap and the ampoule holder (11 in FIG. 2) to each other.

Figure 6:
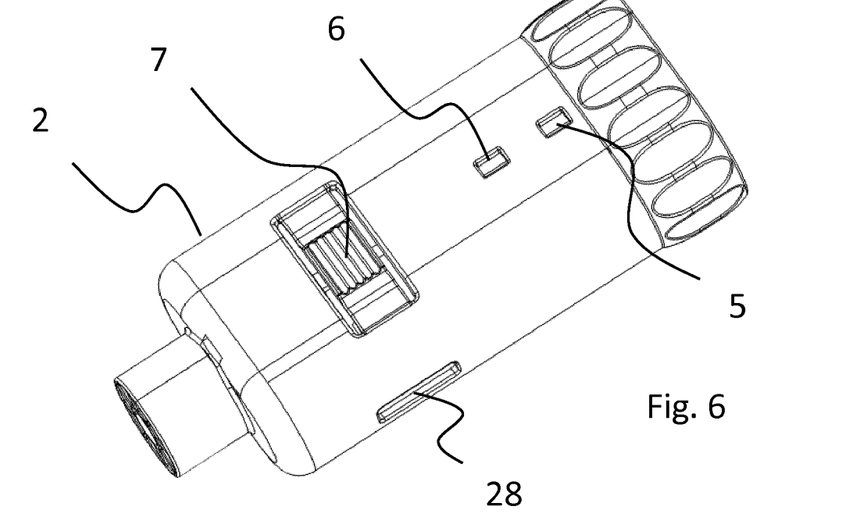
FIG. 6 shows a further perspective view of the housing.

FIG. 6 shows a further perspective view of housing 2. In particular the upper opening 5 for latching the cap illustrated in FIG. 5 in the pre-assembled state and the opening 6 for latching in the actuated state can be seen.

The latching of the cap ensures that the cap can neither be remove nor retracted rearwards by the user in the actuated state without using a tool.

Furthermore, the unlocking means 7 in the form of pushbuttons can be seen, which are formed as an integral component of the housing 2. For this purpose, the housing 2 has slots along the edges of unlocking means 7, so that the profiled unlocking means 7 can be depressed like a button.

Figure 7:
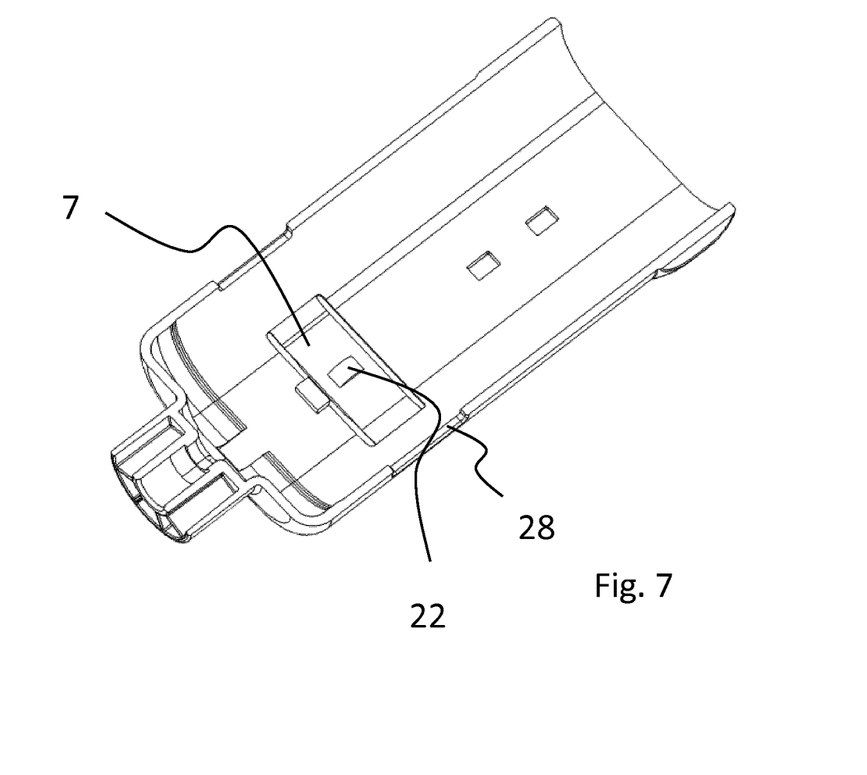
FIG. 7 shows a perspective sectional view of the housing.

FIG. 7 shows a perspective sectional view of the housing. In particular the underside of unlocking means 7 can be seen, where a projection 22 is provided which in the assembled state actuates the latching tabs (18 in FIG. 5) when unlocking means 7 are depressed.

The housing furthermore has lateral openings 28 through which the content of the ampoules is visible for the user, for example.

Figure 8:
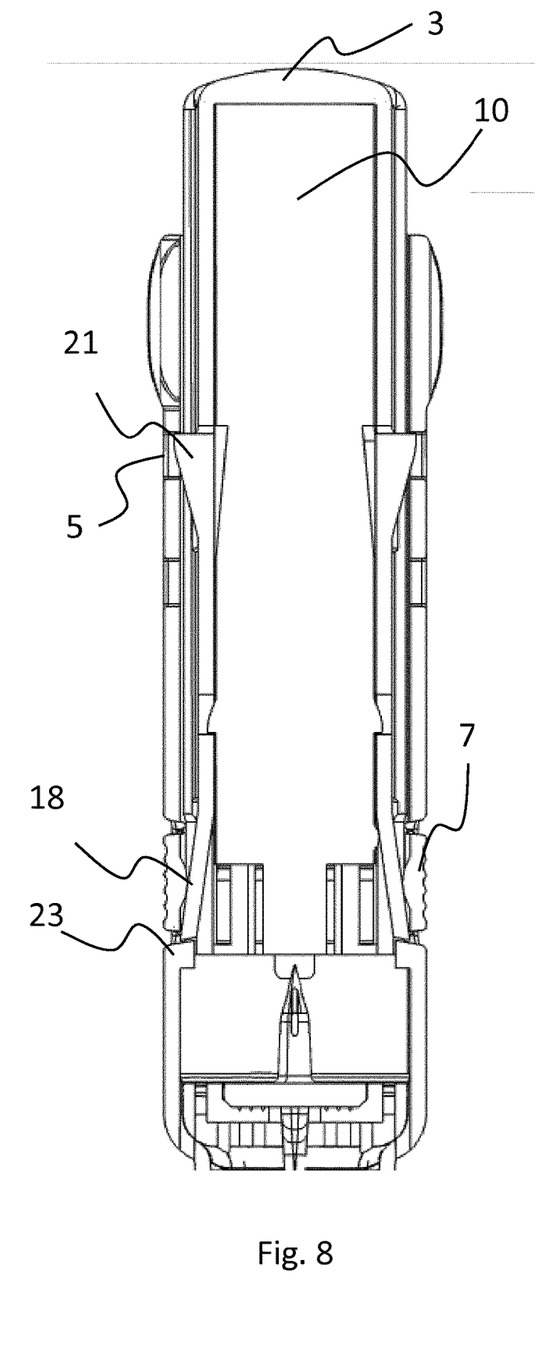
FIG. 8 shows the mixing device in its pre-assembled but not yet actuated state.
Figure 9:
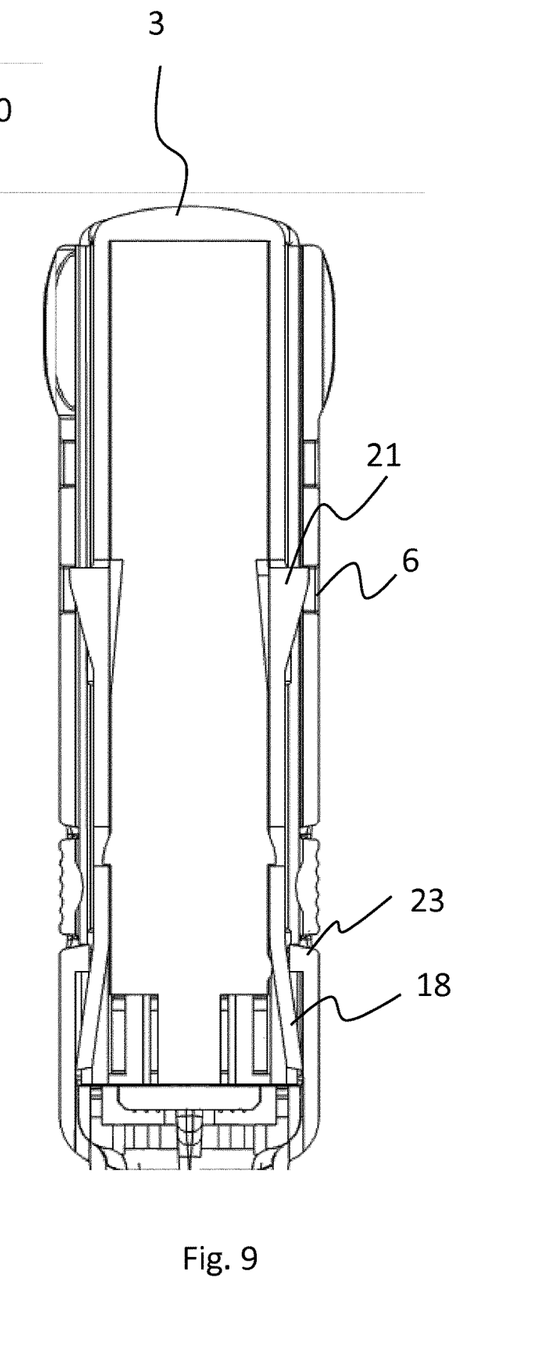
FIG. 9 shows a sectional view in the actuated state.

Referring to FIGS. 8 and 9 which are sectional views, the function of the various latching and locking means will be explained.

FIG. 8 shows the mixing device in its pre-assembled but not yet actuated state.

The ampoules 10 are seated in cap 3.

The cap has latching projections which are locked in an upper opening 5 of the housing and prevent the cap from being retracted.

The front position of cap 3 and hence of the ampoule 10 is delimited by latching tabs 18 which are spread forwardly resting on a collar 23 of the housing.

When the user now actuates the unlocking means 7 by depressing them, the latching tabs 18 will be pressed inwards and can be pushed forward past the collar when the cap is pressed.

The ampoule with the septum is then pressed onto the needle.

FIG. 9 shows a sectional view in the actuated state.

Latching projections 21 are now locked in the lower opening 6 of the housing so that, again, the cap 3 can not be retracted.

The latching tabs 18 have moved past the collar 23.

The front end position may be defined, for example, by abutment of the ampoule against the needle unit.

Figure 10:
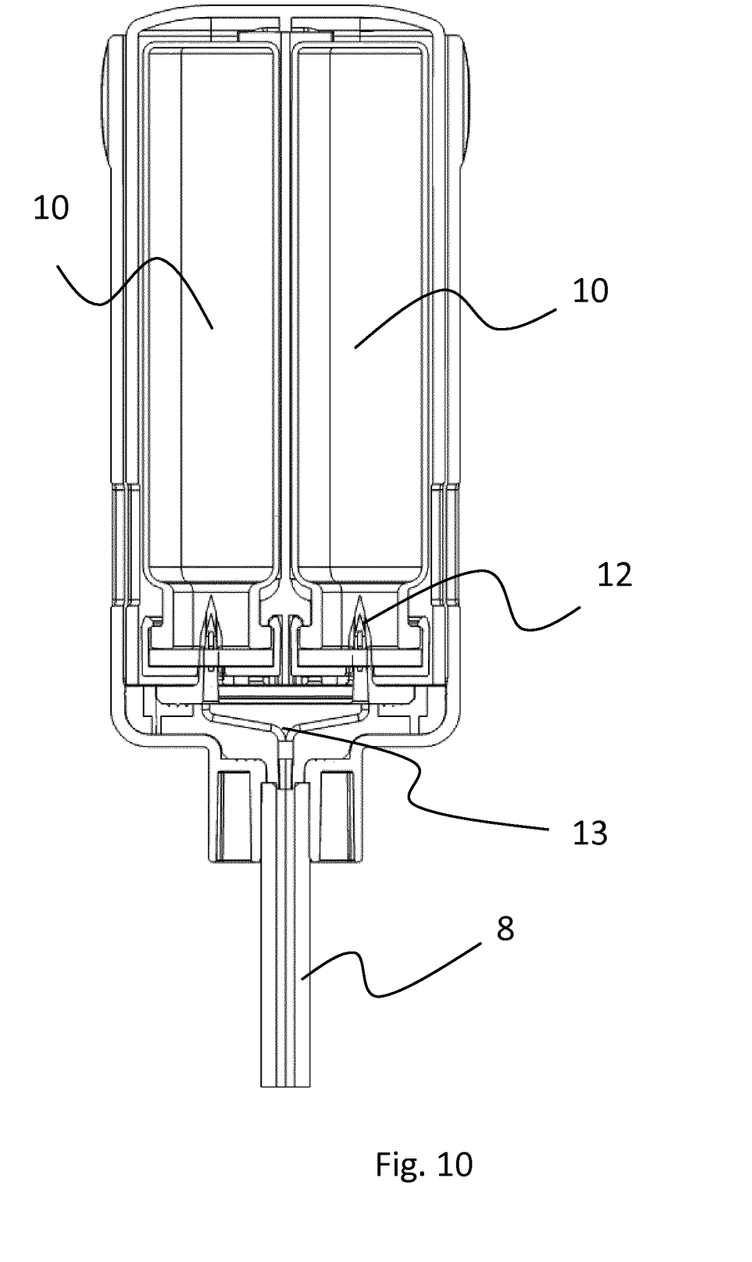
FIG. 10 is a sectional view of the mixing device in the actuated state.

FIG. 10 is a sectional view of the mixing device in the actuated state.

The ampoules 10 with their septum have been pushed onto the needle unit 12. From the needles of needle unit 12, the liquids from the ampoules 10 are flowing into the manifold 13 where they are combined to be discharged via tube 8.

Figure 11:
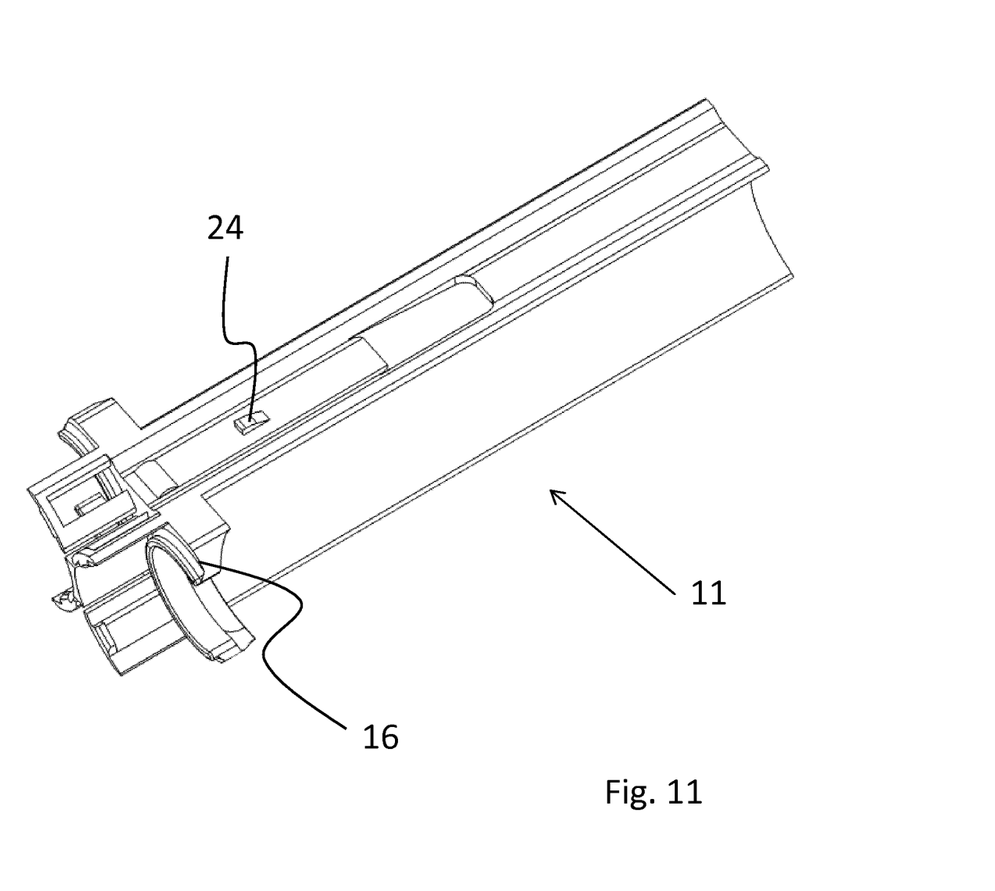
FIG. 11 shows a perspective view of the ampoule holder.

FIG. 11 shows a perspective view of ampoule holder 11.

In particular, the retaining members 16 can be seen, which extend laterally away from the elongated support and are in the form of ring segments into which the ampoules can be snapped.

The holder furthermore has a latching projection 24 which is slideably inserted into the cap, with the holder together with the ampoules.

The latching projection will then lock the holder together with the ampoules in an opening of the cap (20 in FIG. 5).

Figure 12:
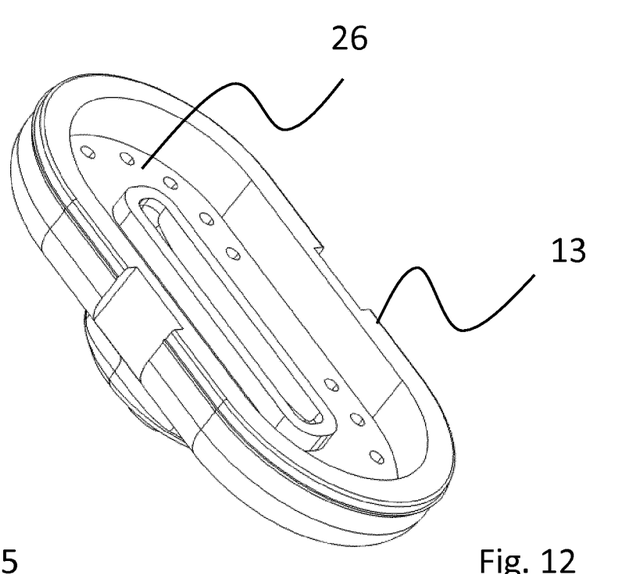
FIG. 12 is a perspective view of the manifold.
Figure 13:
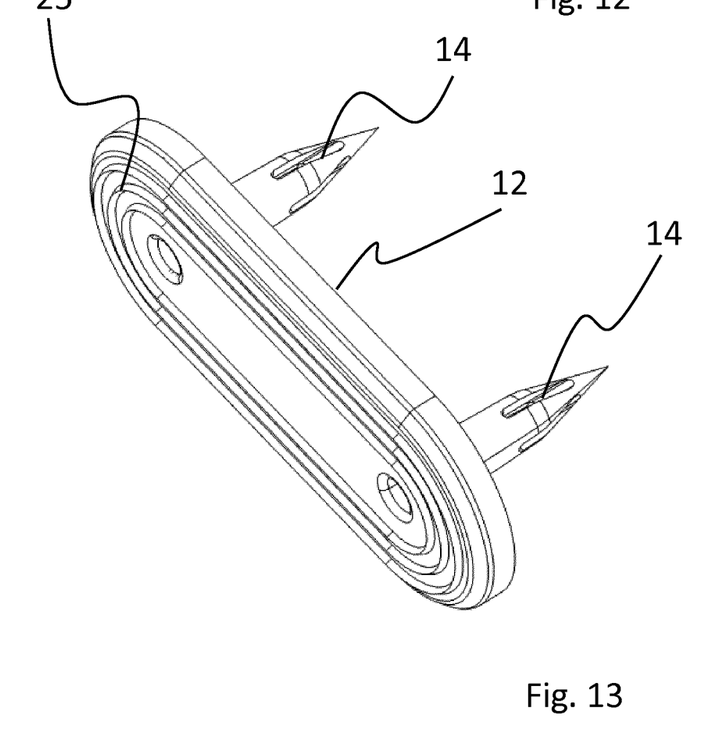
FIG. 13 is a perspective view of the needle unit.

FIGS. 12 and 13 are perspective views of manifold 13 and needle unit 12, respectively.

In the present exemplary embodiment, manifold 13 and needle unit 12 are both made of plastics.

Manifold 13 has a well 26 into which the needle unit 12 is inserted. Needle unit 12 has a profiled surface 25 on its underside, for example in the form of circumferential webs adapted for bonding by ultrasonic welding.

Needles 14 together with the rest of needle unit 12 are formed as a one-piece injection molded component.

In the present exemplary embodiment, needles 14 have a tip and lateral slots extending rearwards of the tip. In this manner, a high flow rate is ensured despite of the use of a plastic component.

Figure 14:
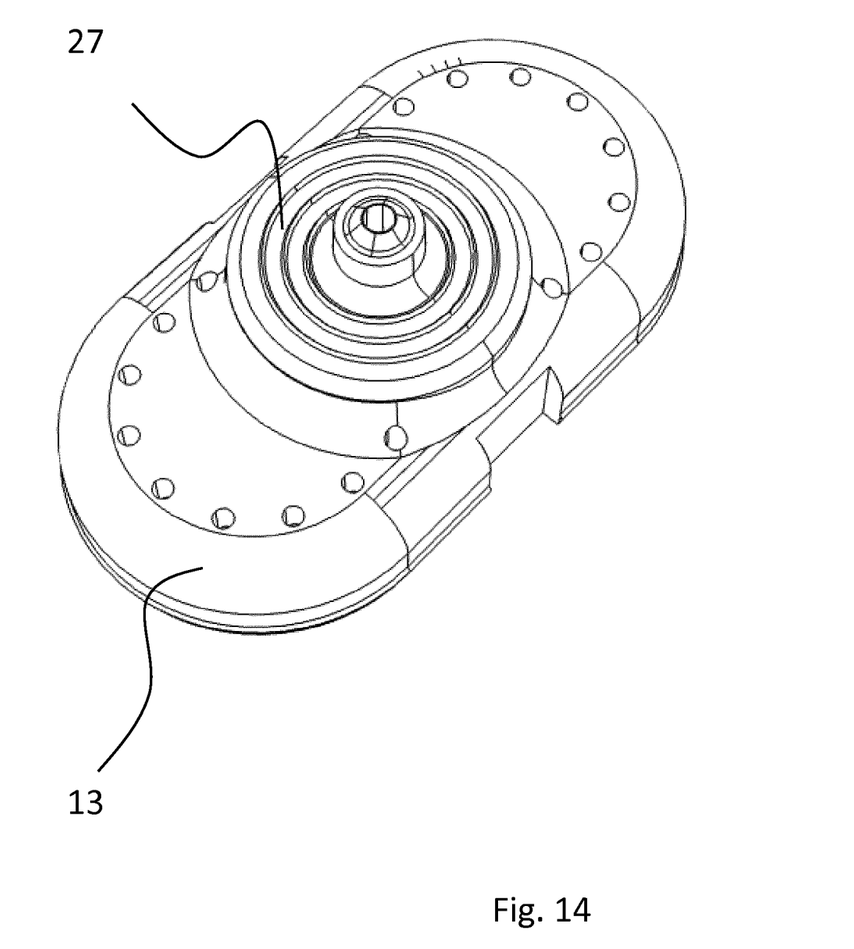
FIG. 14 is a perspective bottom view of the manifold.

FIG. 14 is a perspective bottom view of manifold 13. The underside of manifold 13 also has a profiled surface 27 adapted for welding manifold 13 to the housing of the mixing device.

It will be understood that the subject matter of the invention is not limited to a combination of the features described above, but that a person skilled in the art will in particular combine the features described in conjunction with the drawings as far as technically appropriate.

LIST OF REFERENCE NUMERALS

1 Mixing device
2 Housing
3 Cap
4 Profiled surface
5 Opening
6 Opening
7 Unlocking means
8 Tube
9 Extension
10 Ampoule
11 Ampoule holder
12 Needle unit
13 Manifold
14 Needle
15 Collar
16 Retaining member
17 Septum
18 Latching tab
19 Housing wall
20 Opening
21 Latching projection
22 Projection
23 Collar
24 Latching projection
25 Pattern
26 Well
27 Profiled surface
28 Opening

What is claimed is:

1. A mixing device for bone cement, comprising:
   at least two ampoules filled with a liquid, the liquid comprising a bone cement monomer;
   a housing;
   at least two needles;
   a manifold connected with the housing, the manifold including the at least two needles;
   a slidable ampoule holder in which the at least two ampoules are inserted; and
   a cap;
   wherein, in an engaged position, the at least two ampoules are each perforated by a respective one of the at least two needles and a liquid connection from the at least two ampoules through the at least two needles is established;
   wherein the slidable ampoule holder is latched in the cap;
   wherein the cap is slideably accommodated and latched in the housing;
   wherein the cap projects beyond the housing, at least in a non-engaged position;
   wherein the cap comprises latching projections which are locked in the engaged position in openings of the housing;
   wherein the manifold includes passages for combining the liquids discharged through the needles, the passages merging into a single outlet; and
   wherein the ampoule holder comprises retaining members which extend laterally away from a support and which form ring segments into which the ampoules are snapped.

2. The mixing device as claimed in claim 1, wherein each of the retaining members holds its respective one of the ampoules at a collar of the ampolule.

3. The mixing device as claimed in claim 1, wherein the housing comprises a button to unlock the cap in the non-engaged position.

* * * * *